United States Patent [19]

Kosaka et al.

[11] Patent Number: 4,694,089

[45] Date of Patent: Sep. 15, 1987

[54] PROCESS FOR PREPARING PYROMELLITIC DIANHYDRIDE

[75] Inventors: Tsuneo Kosaka; Yukio Sakai, both of Kurashiki, Japan

[73] Assignee: Mitsubishi Gas Chemical Company, Inc., Tokyo, Japan

[21] Appl. No.: 902,528

[22] Filed: Sep. 2, 1986

[30] Foreign Application Priority Data

Sep. 10, 1985 [JP] Japan .................................. 60-198467

[51] Int. Cl.$^4$ ........................................... C07D 307/89
[52] U.S. Cl. .................................................. 549/239
[58] Field of Search ......................................... 549/239

[56] References Cited

U.S. PATENT DOCUMENTS 2,937,189  5/1960  Hoffman .............................. 549/239

FOREIGN PATENT DOCUMENTS 50-5699  3/1975  Japan .

Primary Examiner—Richard L. Raymond
Attorney, Agent, or Firm—Frishauf, Holtz, Goodman & Woodward

[57] ABSTRACT

A process for preparing pyromellitic dianhydride by dehydration of pyromellitic acid is disclosed. The dehydration is conducted in solid state by indirect heating. The characteristic feature of the process is that when the most part of pyromellitic acid was converted to the dianhydride, the remaining pyromellitic acid is dehydrated while regulating the temperature of the heating medium between 200° C. and 235° C. By this process, pyromellitic dianhydride with excellent quality, good color and free flowing property can be obtained easily, smoothly, and rapidly. A very simple apparatus can be used in the process and the apparatus can be constructed from cheap materials.

11 Claims, No Drawings

PROCESS FOR PREPARING PYROMELLITIC DIANHYDRIDE

BACKGROUND OF THE INVENTION

1. Field of the Invention

This invention relates to a process for the preparation of high-quality pyromellitic dianhydride with a high efficiency by thermal dehydration of pyromellitic acid.

In recent years, due to its unique characteristics, pyromellitic dianhydride is used in a various field as a raw material for super thermal resistant resins. Its typical application is as electronic material.

2. Description of the Prior Art

As to processes for preparing pyromellitic dianhydride by dehydration of pyromellitic acid, there are a process for purifying the product by sublimation concurrently with the dehydration reaction (Japanese Patent Publication No. 5699/1975), a process for effecting the dehydration reaction in a solvent such as acetic anhydride, diphenyl ether, etc., a process for effecting the dehydration in a molten state, and a process for carring out the dehydration in a solid state using a dryer (U.S. Pat. No. 2,937,189).

Among these processes, the sublimation purification process is not satisfactory due to the fact that thermal decomposition is liable to take place and the product is colored since the material is subjected to a relatively high temperature in this process. The process of using acetic anhydride has an advantage in that the material can be homogeneously heated. On the other hand, however, this process has disadvantages, since in the process, recovery of the solvent used is indispensable and it is difficult to eliminate the solvent completely from the product upon completion of the reaction. The process for conducting dehydration in a molten state is not advantageous since it needs a complicate apparatus and it results in deterioration and charring of the product. On the other hand, the process of dehydrating in a solid state is advantageous in that it does not require use of a solvent thus saving procedures for the solvent separation and recovery, and further that it is free from deterioration or decomposition of the compound as long as extremely high temperature is not used.

SUMMARY OF THE INVENTION

In actual practice of this process, however, we have found that although the reaction proceeds very smoothly in the initial phase of dehydration, it does not proceed well in the later phase, especially in the stage of dehydrating pyromellitic acid into the dianhydride in excess of 95% conversion, thus making it impossible to complete the dehydration smoothly.

We have carried out extensive studies for solving the above problem in the solid-state dehydration process, and found that smooth completion of the dehydration reaction can be effected at a lower temperature rather than a high temperature which had been considered to accelerate the dehydration at the final stage. Such a finding has resulted in completion of the present invention.

Thus, the object of this invention is to provide a process for preparing pyromellitic dianhydride from pyromellitic acid by a simple way which can provide smoothly and rapidly the dianhydride with excellent quality and color.

Other objects of this invention will be apparent from the following detailed descriptions.

Accordingly, the characteristic feature of this invention is that in a process for preparing pyromellitic dianhydride by indirect heating of pyromellitic acid with a heating medium, when the most part of the pyromellitic acid was converted to the dianhydride, the remaining pyromellitic acid is dehydrated while regulating the temperature of the heating medium between 200° C. and 235° C.

DETAILED DESCRIPTION OF THE INVENTION

During the first stage in which the most part, e.g. up to 80%, especially 95%, of pyromellitic acid is dehydrated into the dianhydride, heating temperature is maintained at a high level, desirably above 240° C., since dehydration proceeds more efficiently when there is a larger temperature difference between solid pyromellitic acid and heating surfaces. However, it should be noted that the process of this invention is conducted in a solid state and therefore, the formation of a melt should be avoided. Accordingly, in this stage of dehydration, it is desirable to set the temperature of a heating medium below the melting point of pyromellitic acid, i.e. between 240° C. and 275° C. In contrast, in the subsequent stage in which the dehydration ratio of pyromellitic acid has reached at a high level, e.g. 95% or more, a higher temperature gives a detrimental effect on the dehydration efficiency. Thus, the temperature of the heating medium at this stage should be maintained between 200° C. and 235° C., preferably between 220° C. and 230° C.

Therefore, this invention relates to a process for preparing pyromellitic dianhydride by indirect heating of pyromellitic acid with a heating medium which comprises heating and dehydrating the pyromellitic acid while maintaining the temperature of the heating medium not lower than 240° C. until the most part of the acid is converted to the dianhydride, and heating and dehydrating the remaining pyromellitic acid while regulating the temperature of the heating medium between 200° C. and 235° C.

As to the pyromellitic acid used in the process of this invention, any pyromellitic acid obtained by any process such as nitric acid oxidation, oxidation in an aqueous solvent or other liquid phase oxidation of durene can be used. Beside them any other pyromellitic acid may be used. In order to produce high quality pyromellitic dianhydride, those pyromellitic acids purified by means of purification treatment such as recrystallization from water are preferred.

As the heating medium, any kind of heating media generally in use may be employed. Preferred examples of such media include organic heating media such as Dowtherm, Mobiltherm, Marlotherm, diphenyl type heating medium, triphenyl type heating medium, Therm-S (Shin-nippon Seitetsu Kagaku-kogyo Co., Ltd.), KSK-oil (Developed by Kureha Kagaku Co., Ltd. and Sohken Kagaku Co., Ltd.), etc. and inorganic salts such as niter (mixture of $NaNO_2$, $KNO_3$ and $NaNO_3$), etc.

For the dryer for heating and dehydrating pyromellitic acid, any type of apparatus may be suitably used so long as it is capable of heating solid material uniformly. They may be a fluidized bed type dryer equipped with indirect heating means, a paddle type dryer equipped with indirect heating means, a rotary type dryer equipped with indirect heating means, etc., wherein indirect heating means may be any type such as jacket, heating tubes, fin tubes, etc. The process of this invention can be carried out in batch-wise, semi-batch-wise or continuously. Dehydration may be carried out under normal pressure or either under increased or reduced pressure. In view of simplicity of the apparatus to be employed and efficiency of water removal from the system, however, normal or reduced pressure is preferred. To assist the removal of water vapor evolved, it is preferable to pass an inert gas stream such as nitrogen gas, etc. into the dryer.

Although, the reasons why the process of this invention can provide pyromellitic dianhydride from pyromellitic acid so rapidly and smoothly are not yet sufficiently clarified, but at present, we consider as follows:

When the dehydration is conducted at a high temperature, dehydration occurs rapidly from the periphery of the pyromellitic acid particles, and high temperature dehydration gives a shell or skin type structure to the particles. It may be considered that the shell or skin type structure would disturb the diffusion of water vapor evolved from inside of the particles. Contrary to this, when dehydration is conducted at a lower temperature, dehydration would proceed uniformly throughout the volume of the particles. In a dehydration reaction, diffusion velocity of water vapor may be a key factor to conduct the reaction smoothly. If the thickness of the shell or skin is not so large, it would not result so much resistance for diffusion. For example, if the particle shape is assumed as a sphere, and when the thickness of shell reaches one fourth of the diameter of the particle, 88% conversion is already achieved, as the volume of sphere is governed by cubic of diameter. The thickness of shell will rapidly increase when the conversion exceeds over 95%. In the process of this invention, the growth of shell is avoided by lowering the temperature of heating medium at the final stage of dehydration. Relative to the consideration described above, we have noted that there is a slight difference in bulk density of the product obtained by high-temperature dehydration and the product obtained by the process of this invention. As an example, when a product obtained by high-temperature dehydration had a bulk density of $1.06 \sim 1.10$ g/cm$^3$, the product obtained by the process of this invention using the same raw material had a bulk density of $1.01 \sim 1.03$ g/cm$^3$.

It is to be noted, however, that the explanations described just above are given for the reference purposes only and of course, the invention is not confined by them.

According to the process of this invention, pyromellitic dianhydride with a purity higher than 99% can be produced with ease by regulating the temperature within a specific range at the final stage of dehydration. Further, by the process of this invention, pyromellitic dianhydride with excellent quality and color can easily, smoothly, and rapidly be formed in a form of free flowing particles. The process of this invention can be conducted in a very simple apparatus and a cheap material can be used for constructing the apparatus, since in the process of this invention, it is sufficient only to heat solid particles.

DESCRIPTION OF THE PREFERRED EMBODIMENTS

Example 1

Into a trough type dryer having a size of 0.6 m width, 1.6 m length and 0.7 m depth equipped with a rotor and jacket (total heat transfer area: 5.0 m$^2$), 236 kg of purified anhydrous pyromellitic acid containing 0.4 wt% of free water was charged.

A heating medium maintained at a temperature of 165° C. had been circulated through the dryer in advance, and the rotor had been allowed to run at 35 rpm. Further, dry nitrogen gas had been kept to pass through the dryer at a rate of 2 Nm$^3$/hr, so as to prevent the reverse reaction from occurring due to the water formed by the dehydration reaction.

Upon completion of charging pyromellitic acid, temperature of the heating medium was raised to 245° C. Assuming that the dehydration reaction would start at the time when the temperature of pyromellitic acid has reached 180° C., samples were taken from that time on at appropriate intervals for subjecting them to analysis for determining the conversion rate, i.e. the rate of dehydration. The results are shown in Table 1.

TABLE 1

| Dehydration time | Temperature of heating medium | Temperature of PMA[1] & PMDA[2] | Conversion |
| --- | --- | --- | --- |
| 2.0 hr | 245° C. | 230° C. | 31.0% |
| 3.0 hr | " | 231° C. | 51.0% |
| 4.0 hr | " | " | 65.0% |
| 5.0 hr | " | " | 80.0% |
| 6.0 hr | " | " | 86.0% |
| 7.0 hr | " | 233° C. | 92.0% |
| 9.0 hr | " | 234° C. | 97.0% |
| 10.5 hr | " | 236° C. | 98.3% |
| 13.5 hr | " | " | 98.5% |
| 22.8 hr | " | " | 99.1% |
| 24.4 hr | " | 240° C. | 99.4% |
| 34.6 hr | " | 244° C. | 99.6% |

Note [1] Pyromellitic acid
Note [2] Pyromellitic dianhydride

Pyromellitic dianhydride thus obtained was quite satisfactory in color, content of impurities and conversion, i.e. content of pyromellitic dianhydride. The amount of the recovered dianhydride was 193.4 kg, 95.7% of the theoretical yield.

Example 1 described above is given for the purpose to show a conventional process heretofore known in the art and not within the scope of this invention. Accordingly, Example 1 is a comparative Example.

Example 2

Into the dryer used in Example 1, 216 kg of pyromellitic acid with neither free water nor water of crystallization was charged. The procedures followed were the same as those of Example 1, except that at the initial stage, the temperature of the heating medium was set at 270° C., and the temperature was changed to 240° C. and 220° C. when conversion has reached 70% and 94.4%, respectively. The results are shown in Table 2.

TABLE 2

| Dehydration time | Temperature of heating medium | Temperature of PMA[1] & PMDA[2] | Conversion |
| --- | --- | --- | --- |
| 1.0 hr | 270° C. | 233° C. | 12.9% |
| 1.5 hr | " | 237° C. | 31.5% |
| 2.3 hr | 270° C. → 240° C. | 240° C. | 70.0% |
| 3.5 hr | 240° C. | 230° C. | 90.1% |

TABLE 2-continued

| Dehydration time | Temperature of heating medium | Temperature of PMA[1] & PMDA[2] | Conversion |
|---|---|---|---|
| 4.0 hr | 240° C. → 220° C. | 229° C. | 94.4% |
| 5.5 hr | 220° C. | 216° C. | 98.6% |
| 7.5 hr | " | 217° C. | 99.7% |
| 9.5 hr | " | " | 99.8% |

Note [1] Pyromellitic acid
Note [2] Pyromellitic dianhydride

Pyromellitic dianhydride thus obtained was quite satisfactory in color, content of impurities and conversion, i.e. content of pyromellitic dianhydride. The amount of the recovered dianhydride was 174.6 kg, 94% of the theoretical yield.

Example 3

Into the same dryer as used in Example 1, 236 kg of pyromellitic acid with neither free water nor water of crystllization was charged. Procedures for dehydration were similar to those of Example 1 except that the temperature of the heating medium was set at 240° C. at the beginning of the dehydration reaction and the temperature of the heating medium was changed from 240° C. to 225° C. at the time when 80% of conversion was achieved. The results are shown in Table 3.

TABLE 3

| Dehydration time | Temperature of heating medium | Temperature of PMA[1] & PMDA[2] | Conversion |
|---|---|---|---|
| 2.0 hr | 240° C. | 227° C. | 31.5% |
| 4.0 hr | " | " | 63.0% |
| 5.0 hr | 240° C. → 225° C. | " | 80.0% |
| 7.0 hr | 225° C. | 216° C. | 88.0% |
| 8.5 hr | " | 217° C. | 94.5% |
| 11.5 hr | " | " | 99.7% |
| 14.5 hr | " | " | 99.8% |
| 19.5 hr | " | " | 99.9% |

Note [1] Pyromellitic acid
Note [2] Pyromellitic dianhydride

The amount of recovered pyromellitic dianhydride was 193.0 kg, 95% of the theoretical yield. Pyromellitic dianhydride thus obtained was quite excellent in quality and color.

As apparent from the comparison of Examples 1~3, the time required to reach conversion exceeding 99.5% from the conversion of 95% are as follows:

In Example 1, it was more than 15 hours.

24.4 hr (99.4%) − 9.0 hr (97.0%) = 15.4 hr

In Example 2, it was less than 3.5 hours.

7.5 hr (99.7%) − 4.0 hr (94.4%) = 3.5 hr

In Example 3, it was less than 3.0 hours.

11.5 hr (99.7%) − 8.5 hr (94.5%) = 3.0 hr

Further, the total hours to achieve conversion exceeding 99.5% are about 30 hours in Example 1, about 7 hours in Example 2, and about 11 hours in Example 3.

Based on the results described above, it is apparent that the process of this invention is far superior to conventional processes.

We claim:

1. A process for preparing pyromellitic dianhydride by indirect heating of pyromellitic acid with a heating medium, which comprises heating and dehydrating the pyromellitic acid in a solid state while maintaining the temperature of the heating medium not lower than 240° C. until about 80% to about 95% of the acid is converted to the dianhydride, and heating and dehydrating the remaining pyromellitic acid while regulating the temperature of the heating medium between 200° C. and 235° C.

2. The process as claimed in claim 1, wherein about 95% of the acid is converted.

3. The process as claimed in claim 1, wherein the dehydration is conducted within a trough type dryer.

4. The process as claimed in claim 1, wherein the dehydration is conducted while passing nitrogen gas through the dryer.

5. A process for preparing pyromellitic dianhydride by indirect heating of pyromellitic acid with a heating medium, which comprises heating and dehydrating the pyromellitic acid in a solid state while maintaining the temperature of the heating medium of from 240° C. to the melting point of the acid until about 80% to about 95% of the acid is converted to the dianhydride, and heating and dehydrating the remaining pyromellitic acid while regulating the temperature of the heating medium between 220° C. and 230° C.

6. The process as claimed in claim 5, wherein about 95% of the acid is converted.

7. The process as claimed in claim 5, wherein the dehydration is conducted within a trough type dryer.

8. The process as claimed in claim 5, wherein the dehydration is conducted while passing nitrogen gas through the dryer.

9. The process of claim 1 wherein a temperature range of 240° C. to 275° C. is maintained during the conversion of 80 to 95% of the acid to dianhydride.

10. The process of claim 9 wherein the remaining pyromellitic acid is dehydrated in the temperature range of 220° C. to 230° C.

11. The process of claim 10 wherein 95% of the acid is converted by heating in the 240° C. to 275° C. temperature range.

* * * * *